(12) United States Patent
Butler et al.

(10) Patent No.: US 6,511,964 B2
(45) Date of Patent: Jan. 28, 2003

(54) METHOD FOR TREATING ACUTE MOUNTAIN SICKNESS

(75) Inventors: Terri L. Butler, Kirkland, WA (US); John St. Cyr, Coon Rapids, MN (US); Clarence A. Johnson, Wyoming, MN (US)

(73) Assignee: Bioenergy, Inc., Ham Lake, MN (US)

( * ) Notice: Subject to any disclaimer, the term of this patent is extended or adjusted under 35 U.S.C. 154(b) by 0 days.

(21) Appl. No.: 09/821,238

(22) Filed: Mar. 29, 2001

(65) Prior Publication Data

US 2002/0065232 A1 May 30, 2002

Related U.S. Application Data

(63) Continuation-in-part of application No. 09/406,266, filed on Sep. 24, 1999, now Pat. No. 6,218,366.

(51) Int. Cl.$^7$ ................................................ A61K 31/70
(52) U.S. Cl. ........................................................ 514/23
(58) Field of Search ............................................ 514/23

(56) References Cited

U.S. PATENT DOCUMENTS

| | | | | |
|---|---|---|---|---|
| 5,101,819 A | * | 4/1992 | Lane | 128/204.18 |
| 5,856,331 A | * | 1/1999 | Bursten et al. | 514/263 |
| 6,159,942 A | | 12/2000 | St. Cyr et al. | 514/23 |
| 6,159,943 A | | 12/2000 | Butler et al. | 514/23 |
| 6,218,366 B1 | | 4/2001 | St. Cyr et al. | 514/23 |
| 6,296,892 B1 | * | 10/2001 | Elseviers et al. | 426/653 |

* cited by examiner

*Primary Examiner*—James H. Reamer
(74) *Attorney, Agent, or Firm*—Schwegman, Lundberg, Woessner & Kluth, P.A.

(57) ABSTRACT

Persons encountering high altitudes without being acclimatized can prevent or alleviate the symptoms of acute mountain sickness by administration of ribose one to four times a days, beginning immediately on encountering high altitudes and continuing for at least five days.

4 Claims, No Drawings

METHOD FOR TREATING ACUTE MOUNTAIN SICKNESS

CROSS-REFERENCE TO RELATED APPLICATIONS

This application is a continuation-in-part of U.S. patent application Ser. No. 09/406,266, filed on Sep. 24, 1999, now U.S. Pat. No. 6,218,366, which is incorporated herein by reference.

FIELD OF THE INVENTION

The present invention relates to compositions and methods for treating acute mountain sickness.

BACKGROUND OF THE INVENTION

It is well known that the energy coinage of the cell is adenosine triphosphate (ATP). During anabolism, the energy derived from the metabolism of nutrients is transferred to high energy phosphate bonds of ATP. The energy in these bonds is expended during the energy consumption phase. An important and "costly" expenditure, in which ATP is rapidly cycled, is that required for muscular contraction.

The energy buildup steps occur within the muscle cell during two basic processes. Oxidative phosphorylation replenishes ATP by the breakdown of circulating fatty acids, glucose and intramuscular glycogen and triglycerides. Anaerobic phosphorylation provides ATP from creatine phosphate, circulating glucose and intramuscular glycogen via kinase reactions such as the myokinase reaction.

In the synthesis of ATP via the nucleotide salvage pathway, the nucleotide precursors that may be present in the tissue are converted to AMP and further phosphorylated to ATP. Adenosine is directly phosphorylated to AMP, while xanthine and inosine are first ribosylated by 5-phosphoribosyl-1-pyrophosphate (PRPP) and then converted to AMP. Ribose is found in the normal diet only in very low amounts, and is synthesized within the body by the pentose phosphate pathway. In the de novo synthetic pathway, ribose is phosphorylated to PRPP, and condensed with adenine to form the intermediate adenosine monophosphate (AMP.) AMP is further phosphorylated via high energy bonds to form adenosine diphosphate (ADP) and ATP. During energy consumption, ATP loses one high energy bond to form ADP, which can be hydrolyzed to AMP. AMP and its metabolites adenine, hypoxanthine and inosine are freely diffusible from the muscle cell and may not be available for resynthesis to ATP via the salvage pathway.

In U.S. Pat. No. 4,719,201, it is disclosed that when ATP is hydrolyzed to AMP in cardiac muscle during ischemia, the AMP is further metabolized to adenosine, inosine and hypoxanthine, which are lost from the cell upon reperfusion. In the absence of AMP, rephosphorylation to ADP and ATP cannot take place. Since the precursors were washed from the cell, the nucleotide salvage pathway is not available to replenish ATP levels. It is disclosed that when ribose is administered via intravenous perfusion into a heart recovering from ischemia, recovery of ATP levels is enhanced.

The availability of PRPP appears to control the activity of both the salvage and de novo pathways, as well as the direct conversion of adenine to ATP. Production of PRPP from glucose via the pentose phosphate pathway appears to be limited by the enzyme glucose-6-phosphate dehydrogenase (G6PDH). Glucose is converted by enzymes such as G6PDH to ribose-5-phosphate and further phosphorylated to PRPP, which augments the de novo and salvage pathways, as well as the utilization of adenine. The addition of ribose bypasses this rate limiting enzymatic step.

Many conditions produce hypoxia. Such conditions include acute or chronic ischemia when blood flow to the tissue is reduced due to coronary artery disease or peripheral vascular disease where the artery is partially blocked by atherosclerotic plaques. Transient hypoxia frequently occurs in individuals undergoing anesthesia and/or surgical procedures in which blood flow to a tissue is temporarily interrupted. Peripheral vascular disease can be mimicked in intermittent claudication where temporary arterial spasm causes similar symptoms.

Persons encountering high altitudes or the effective high altitude conditions of air travel, may become hypoxic. They are additionally subjected to low atmospheric pressure. The combination of these two conditions results in Acute Mountain Sickness (AMS). Headache is perhaps the most common symptom of AMS. Headache may be accompanied by lethargy and in extreme cases, potentially fatal cerebral edema. Lung tissue is also affected. Shortness of breath is common and potentially fatal pulmonary edema can occur. Many subject experience nausea. If the symptoms are severe, the person must be taken immediately to lower altitudes and may require hospitalization. If the symptoms are mild, the person may choose to tolerate the discomfort.

A continuing need exists for compositions and methods to alleviate or prevent the symptoms of acute mountain sickness.

SUMMARY OF THE INVENTION

The present invention provides compositions for, and methods to, alleviate or prevent the symptoms of acute mountain sickness, which include headache, nausea, lethargy and pulmonary edema with associated shortness of breath and cough. It is believed that the present compositions and methods allow mammals to tolerate situations in which, absent the present compositions and methods, the mammal would experience the onset of symptoms of AMS. The preferred compositions include D-Ribose alone or, optionally, in combination with other energy pathway intermediates, oxygenating substances or pharmaceuticals in pharmaceutically acceptable carriers.

It is here shown that the administration of ribose will alleviate or prevent the symptoms of AMS. Ribose is preferably administered before and during exposure to high altitudes or simulated high altitudes. Preferably, ribose is administered fifteen minutes before exposure to high altitude and two or three times a day until the subject is acclimated to high altitudes. The usual subject becomes acclimated in about five days and ribose can be discontinued at that time. If symptoms re-occur, ribose administration should be re-instituted. Many subjects may choose to take ribose throughout their stay at high altitudes. Ribose is administered in single doses of 0.5 to 30 grams, preferably in doses of three to ten grams, and most preferably in a dose of five grams. The ribose can be administered in any convenient form, such as dissolved in water, added to a soft drink, sprinkled on dry food or incorporated into bars.

DETAILED DESCRIPTION OF THE INVENTION

The present invention provides a method of alleviating the symptoms of acute mountain sickness (AMS) of a human, by the oral, intravenous or peritoneal administration of and effective amount of ribose to said human. AMS commonly occurs in persons going abruptly from near sea level to a higher elevation. Depending on individual susceptibility, AMS can occur at relatively low altitudes. Persons who are exposed to, for example, carbon monoxide from smoking, or persons with preexisting conditions such as asthma are among those groups that are particularly susceptible to AMS. Altitudes above about 1,000 meters are at significantly lower oxygen tension and atmospheric pressure than at sea level and such more susceptible persons may begin experiencing AMS at this altitude. At altitudes between 1,500 and 3,000 meters, up to 25% of unacclimatized travelers experience AMS. At higher altitudes, both the incidence and severity of AMS increase.

AMS is characterized by a constellation of symptoms. Headache is the main symptom. Nausea, vomiting, dyspnea, insomnia, lethargy, loss of energy, impaired cognition and balance. The onset of symptoms typically occurs within hours to three days after arrival at the high altitude. These symptoms may resolve after several days, but can lead to fatal conditions of cerebral edema and pulmonary edema. Even those experiencing no or minimal symptoms at rest will be more affected if they attempt to exercise.

Travelers who are able to acclimatize gradually, preferably at several stages of increasing altitude, are less affected by AMS. If slow acclimatization is not possible, several medications have been used for the prevention or amelioration of AMS. Acetazolamide is a carbonic anhydrase inhibitor, which creates a metabolic acidosis due to a renal loss of bicarbonate and an inhibition of red blood cell enzymes with a retention of carbon dioxide. If acetazoamide is taken daily, starting three days before reaching altitude, sleep is improved, exercise performance is improved and higher altitudes can be tolerated. Dexamethasone is a catabolic steroid that is effective in reducing vasogenic cerebral edema. It has been found to reduce the symptoms of AMS due to exposure to very high altitudes. Nifedipine, a calcium-channel blocker, may prevent pulmonary problems. The usefulness of these two agents at intermediate altitudes is unclear.

Many persons travel to high altitudes expressly for the purpose of sports, such as skiing and golf. Others are exposed to airplane cabin pressures that are equivalent to altitudes of 2,000 to 4,000 meters for flights as long as eight to twelve hours. All of these subjects would benefit from an easily obtainable, non-prescription agents that would enable them to exercise more comfortably without incurring the headache, lethargy or more severe symptoms of AMS. It has been found as a preliminary result that various persons exercising at high altitudes felt more energetic and did not have AMS when ingesting ribose.

It must be cautioned that persons cannot rely on the compositions and methods of this invention to prevent or give total relief to AMS. If symptoms are severe, it is imperative to evacuate the person to lower altitudes and professional medical care.

For the purpose of describing this invention, the following terms have the following meanings:
1. "Ribose" means a monosaccharide, including but not limited to, ribose, and any 5-carbon precursor of ribose, D-ribose, ribulose, xylitol and xylulose.
2. "Hypoxia" means any state in which the tissue oxygen saturation is reduced to a less than optimal level. Hypoxia includes anoxia, ischemia and poisoning with toxic agents such as carbon monoxide and cyanide which interfere with oxygen utilization. Hypoxia may be chronic as in congestive heart failure, coronary artery disease, peripheral vascular disease or pulmonary dysfunction, or transient as in anesthesia, surgical procedures or exposure to high altitudes.
3. "Hypoxic threshold" is that basal level where oxygen saturation of tissues is less than optimal. A raised hypoxic threshold increases tolerance to situations which would otherwise result in hypoxia.
4. "Ischemia" is that state of hypoxia caused by reduced circulation of blood to tissue.
5. "Acute mountain sickness" (AMS) is the condition brought on exposure by low oxygen tension combined with low atmospheric pressure. AMS occurs when mammals are brought suddenly to high altitudes, without acclimatization. AMS can also occur on long airplane flights which simulate high altitude.

In co-pending patent application Ser. No. 09/290,789 (the "'789 Application"), now U.S. Pat. No. 6,159,942, the teaching of which is hereby incorporated by reference, it is disclosed that administration of D-ribose increases the energy level of mammals by stimulating the synthesis of ATP. Examples therein show that ATP levels in the skeletal muscle of healthy mammals under normal conditions of oxygen availability increase upon ribose administration and that the increase is correlated with an increase in performance and activity levels. It is also shown that administration of D-Ribose provides some benefit even to patients with coronary artery disease.

The invention described in the parent to this application, U.S. patent application, Ser. No. 09/406,266, filed Sep. 24, 1999, now U.S. Pat. No. 6,218,366 the teaching of which is hereby incorporated, was based on the discovery that administration of ribose can also increase the tolerance of tissue to low oxygen availability, that is, to hypoxia. In patients with ischemic heart disease, regions of the heart may be poorly perfused, dysfunctional, but still viable. Myocardial ischemia limits blood flow and therefore the available supply of oxygen. This limited availability of oxygen affects oxidative metabolism, which ultimately negatively affects the production of ATP, essential for maintenance of contractility and cellular integrity. Varied states of ischemia exist. However, either transient or chronic ischemia may result in partial reduction of myocardial ATP with subsequent impairment of contractile function, which can lead to heart failure but not cell death.

Therapeutic intervention is variable and must be tailored to each patient. Non-surgical therapies may offer a primary mode of treatment. The first line of action includes angiotensin-converting inhibitors, digoxin and diuretics. So-called inotropic agents such as dobutamine, arbutamine, dopamine, amrinone and milronine, which increase stroke volume and cardiac output, have been universally used for treatment of cardiac dysfunction, which can be manifested by edema, dyspnea, pulmonary congestion and organ hypoperfusion. Many previous studies have investigated the use of ribose in healthy animals such as dogs, rats and swine that have been subjected to ischemic insult. While such studies may suggest therapies for humans with cardiovascular disease, Energy and oxygen availability can each independently influence tissue integrity and function. Although ribose has been shown to enhance energy levels under conditions of normal oxygen availability, the present invention surprisingly shows that when ribose is present, tissue can endure low oxygen availability while still maintaining normal function, without being subjected to the deleterious effects due to low oxygen. Even if energy is available in sufficient quantities, but oxygen is low, adverse effects may still occur in the hypoxic tissue. These effects include pH changes, imbalance in intermediate metabolites and the like.

In other words, ribose ameliorates the effects of hypoxia, that is, it raises the hypoxic threshold.

Many patients suffering from "silent" cardiovascular disease, that is, such patients are unaware of their condition of chronic hypoxia. The treadmill test has been extensively used to raise the oxygen demand of the heart and uncover the low hypoxic threshold. However, treadmill testing may not be the test of choice in all situations. Dobutamine has been found particularly useful for simulating exercise in patients with coronary artery disease. The infusion of dobutamine produces a stressful myocardial condition similar to that produced by exercise, while the patient is in a controlled hospital setting, with intravenous infusion, in which intervention is readily available. It is theorized that dobutamine increases myocardial stroke volume and cardiac output while reducing ventricular volume and mitral regurgitation due to its vasodilating effects. Because of these multiple effects, dobutamine has been investigated extensively as an agent to increase sensitivity in identifying segmental wall motion activity by echocardiography.

One of the causative factors of AMS is hypoxia and some of the symptoms of AMS are common to those of hypoxia at sea level. It may be expected therefore that the administration of ribose would alleviate lethargy. However, hypoxia does not normally cause headache, cerebral edema, nausea and pulmonary edema. The present invention is directed to amelioration or prevention of the symptoms of AMS, wherein the stress of low oxygen tension is compounded by low atmospheric pressure, which deleteriously affects breathing, leading to pulmonary edema with accompanying cough and edema. The following examples illustrate but are not intended to limit the invention.

EXAMPLE 1
Use of D-Ribose Plus Dobutamine

A. Echocardiography

A single-center, randomized, double-blind placebo-controlled clinical trial was carried out to evaluate the safety and efficacy of D-Ribose on myocardial wall motion during echocardiographic examination in patients suspected of having stunned or hibernating myocardium.

Patients included:
- ages 18 or older, male or female
- stable resting wall motion abnormalities noted on baseline echocardiography, defined as at least two segments with abnormal function.
- at least five days from a major cardiac event such as myocardial infarction or unstable angina
- no known allergies or contraindications to D-Ribose or dobutamine
- stable medical regimen of vasoactive medications
- known coronary artery disease (CAD) discovered by cardiac catheterization, myocardial infarction or positive stress test

OR

- patients with high index of suspicion for CAD provided they have a resting wall abnormality on ECHO
- for females of child-bearing potential, a negative pregnancy test
- signed informed consent approved by an Institutional Review Board Patients excluded:
- diabetes mellitus requiring insulin or an oral hypoglycemic agent
- inability to sign consent form
- history of non-ischemic cardiomyopathy
- clinically significant liver or renal disease in the judgment of the investigator
- advanced valvular heart disease in the judgment of the investigator Patients were randomized into placebo and ribose groups according to a computer generated randomization schedule. The identity of the contents was blinded to the investigator. Patients were identified by initials. The selected study population was comprised of 25 patients (22 men and 3 women) with a mean age of 57+/−11 years. All had reduced left ventricular systolic function (mean ejection fraction 30+/−8%, range 18 to 48%). Twenty-two patients (88%) had prior myocardial infarction and only one subject was evaluated after recent (<4 weeks) infarction. Nineteen patients (76%) had stable angina pectoris and 21 (84%) were receiving one or more medications to treat ischemia (nitrates (21), beta-antagonists (9), calcium channel antagonists (9)). Coronary artery disease (>=50% diameter stenosis) was documented by angiography in 22 patients. Of the 21 who had recent studies, 12 had three-vessel, 8 had two-vessel and one had single vessel disease. Subjects were admitted to the hospital on the morning of study day 1 after an 8 hour fast. After a limited physical examination, a baseline (AM) echocardiogram was obtained. Following the imaging study, continuous monitoring of the heart rhythm was initiated.

After completion of the baseline echocardiography, intravenous infusion of test agent (D-Ribose or placebo) at a set infusion, along with an infusion of 5% glucose in water (D5W) at 100 ml/hour as a maintenance fluid was initiated. D-Ribose, 10% in water at 180 mg/kg/hour, or placebo D5W at 1.8 mg/kg/hour, were given as sterile, pyrogen-free solutions. After the test agent had been administered for one, two, three or four hours, a resting echocardiogram was obtained. At completion of this rest period, dobutamine was infused. Dobutamine hydrochloride (Dobutrex® solution, Eli Lilly, Indianapolis) was mixed in D5W (5% dextrose in water), giving a concentration of 1.0 mg/ml. During echocardiography, dobutamine was administered at an initial dose of 5 $\mu$g/kg/minute for three minutes. The dose of dobutamine was then increased to 10 $\mu$g/kg/min and infused for three minutes. Echocardiograms were obtained at the low dose stages and at peak stage. Every three minutes the concentration of dobutamine was increased by 10 $\mu$g/kg/minute increments until the standard endpoint was reached. The standard endpoint was set to be $\geq$2 mm ST-segment depression on ECG; significant side effects or arrhythmias; achievement of 85% of the age-predicted maximal heart rate; a systolic blood pressure >250 mm Hg, a significant fall in systolic blood pressure or a maximal dose of 50 $\mu$g/kg/minute.

Post-infusion images were recorded approximately eight minutes after discontinuation of dobutamine. Upon completion of imaging, the test article infusion was terminated. Subjects were observed overnight and on Day 2 were crossed over to the alternate test article. Study protocols on Day 2 were identical to those of Day 1.

B. Echocardiographic Analysis

Baseline (AM) and PM two-dimensional echocardiograms and any post-revascularization studies were performed using an Advanced Technology Laboratories UM9 HDI (Bothell, Wash.) with a 3.0 MHZ phased array transducer and a Hewlett Packard Sonos 1500 (Andover, Mass.) with a 2.5 MHZ phased array transducer. Parasternal long and short-axis and apical two and four-chamber images were recorded on 0.5 inch videotape and digitally stored on floppy discs using a Nova MicroSonics DCR or Colorvue system (Mahwah, N.J.). End-diastolic and systolic images were acquired on line at 67 msec intervals.

The Day 1 and Day 2 AM and PM echocardiograms for each subject were transferred from floppy disk to a customized image network where each subject's images were archived only by hospital number. The images were retrieved from the network and analyzed using the Indiana University Off-line Revue System. Once retrieved, the images were rearranged in computer memory to display AM and PM images side by side for each echocardiogram view. Two blinded investigators rendered a consensus interpretation of regional wall motion in 16 left ventricular segments. Wall motion was graded as: (1) normal; (2) mildly hypokinetic with <5 mm inward systolic motion; (2.5) severely hypokinetic with minimal inward systolic motion and wall thickening; (3) akinetic with an absence of inward motion and wall thickening; (4) dyskinetic with paradoxical outward motion. A global wall motion score was derived for each echocardiogram (sum of individual segment scores per number of segments scored.)

The Day 1 and Day 2 dobutamine echocardiograms comprised of resting, 5, 10 µg/kg/minute, and peak dose images were stored and reviewed using the procedures and equipment previously described for the AM and PM images, except that side by side comparison was not performed. Using the previously described scoring system, regional wall motion was graded by consensus by two blinded investigators. Hyperdynamic wall motion during dobutamine infusion was scored as one normal wall motion. A one grade improvement of wall motion during dobutamine infusion was considered significant. Global wall motion scores were derived for each stage of the dobutamine echocardiogram.

During low-dose dobutamine, wall motion improved in more segments on D-Ribose than placebo (65 segments v. 48 segments). Stress-induced ischemic abnormalities occurred in more segments on placebo than on ribose (43 segments v. 31). Stress-induced abnormalities occurred in more patients on placebo than on ribose (71% v. 46%).

Eleven patients subsequently underwent CABG after completion of Study Day 2. At least one echocardiogram was obtained postoperatively in each of these subjects. Regional wall motion was compared between the follow-up echocardiogram and the Day 1 AM study by two blinded investigators. A single, blinded investigator made determinations of ejection fraction on the AM, PM, dobutamine and any post-revascularization echocardiograms using the four-chamber view and the Simpson's method. As shown in Table VII, the accuracy of dobutamine plus D-Ribose in identifying patients with increase in ejection fraction (EF) after surgery greater than or equal to 5% was 82% compared to 45% of placebo controls.

TABLE VII

Improvement of Ejection Fraction Following CABG

| | Analysis 1: EF Increase ≥ 5% | | Analysis 2: EF Increase ≥ 10% | |
| --- | --- | --- | --- | --- |
| | Ribose | Placebo | Ribose | Placebo |
| Sensitivity | 89% (8/9) | 56% (5/9) | 57% (4/7) | 29% (2/7) |
| Specificity | 50 (1/2) | 0 (0/2) | 100 (4/4) | 25 (1/4) |
| Accuracy | 82 (9/11) | 45 (5/11) | 73 (8/11) | 27 (3/11) |

EXAMPLE 2

Subjects Exercising at High Altitudes

A. A healthy, young man, 22 years of age, is an accomplished skier who frequently travels to high altitudes to pursue his sport. In the past, he has experienced mild AMS symptoms, mainly mild dyspnea. On a ski trip to Breckinridge, Colo., at 10,000 feet altitude, he ingested a dose of about five grams of ribose in water in the morning before going skiing and in the evening after skiing all day. He was surprised that he was not winded during skiing and did not experience soreness in his thighs as he had on past ski trips.

B. Three men, aged 30 to 55 frequently golfed at Vail, Colo., an altitude of 10,000 feet. In the past, they had experienced mild AMS symptoms, including headache, lethargy and nausea. On this trip, each man ingested about five grams of ribose before golfing. At the end of the day, they had no AMS and felt better than on any previous golf trips at high altitude.

C. A man aged 69 and a woman aged 66 frequently traveled to Colorado to ski. Generally, they felt more tired when at high altitudes than at low altitudes. On this trip, they ingested about five grams of ribose dissolved in water each morning before going out to ski and another approximately five grams at the end of the day. They had more energy, increased endurance and better recovery for skiing the next day.

Based on these anecdotal reports, a clinical study will be carried out to provide objective measures of the efficacy of ribose in preventing or ameliorating symptoms of high altitude hypoxia. Six volunteer subjects will be selected for a pilot study. All will be healthy and physically fit. The study will be submitted for approval to the Institution Review Board. Three subjects will ingest five grams of ribose ten minutes before exercise and five grams of ribose immediately after exercise. Three subjects will ingest equal amount of glucose at the same time points. Trials, according to the following protocol, will be run at 1000 feet above sea level and at an elevation of approximately 12,000 feet.

Protocol

Subjects will cycle a ramped protocol consisting of five minute stages and 0.5 kg increases in workload.

Each subject will perform three rides per trial.

The first trial will consist of cycling at the low altitude site (Monday/Tuesday).

For the second trial, subjects will be flown to the high altitude site to repeat the exercise (Saturday).

The subjects will be flown back to the low altitude site for the third trial (Sunday).

Blood samples will be obtained before exercise and at each five minute interval during the trial, and at 30 and 60 minutes post exercise.

Heart rate and RPE will be recorded at the end of each interval.

Parameters measured will be: hemoglobin, cyanomethemoglobin, hematocrit, uric acid, lactic acid, reduced and oxidized glutathione. The data will be analyzed by ANOVA with Tukey's LSD posthoc test to differentiate means.

All of the compositions and methods disclosed and claimed herein can be made and executed without undue experimentation in light of the present disclosure. While the compositions and methods of this invention have been described in terms of preferred embodiments, it will be apparent to those skilled in the art that variations may be applied to the compositions and methods described herein without departing from the concept and scope of the invention. More specifically, it will be apparent that certain agents that are both chemically and physiologically related may be substituted for the agents described herein while the same of similar results would be achieved. All such similar substitutes and modifications apparent to those skilled in the art are deemed to be within the scope and concept of the invention as defined by the appended claims.

We claim:

1. A method to prevent or alleviate the symptoms of acute mountain sickness in a mammal experiencing the symptoms of acute moutain sickness, the method comprising administering an amount of ribose to the mammal effective to prevent or alleviate said symptoms.

2. The method according to claim 1 wherein the subject is a human.

3. The method according to claim 2 wherein ribose is administered in a dosage of about three to ten grams.

4. The method of claim 1 wherein ribose is administered one to four times daily for a period of five days.

* * * * *